(12) United States Patent
Liu et al.

(10) Patent No.: US 9,643,030 B2
(45) Date of Patent: May 9, 2017

(54) HIGH-INTENSITY FOCUSED ULTRASOUND THERMAL ABLATION APPARATUS HAVING INTEGRATED TEMPERATURE ESTIMATION AND ELASTOGRAPHY FOR THERMAL LESION DETERMINATION AND THE METHOD THEREOF

(75) Inventors: Hao-Li Liu, Tao-Yuan County (TW); Ming-Shi Lin, Taitung County (TW)

(73) Assignee: CHANG GUNG UNIVERSITY, Tao-Yuan (TW)

(*) Notice: Subject to any disclaimer, the term of this patent is extended or adjusted under 35 U.S.C. 154(b) by 583 days.

(21) Appl. No.: 12/926,326

(22) Filed: Nov. 10, 2010

(65) Prior Publication Data
US 2011/0306881 A1  Dec. 15, 2011

(30) Foreign Application Priority Data

Jun. 9, 2010  (TW) .............................. 099118654 A

(51) Int. Cl.
  *A61B 8/00*  (2006.01)
  *A61N 7/02*  (2006.01)
  *A61B 8/08*  (2006.01)
  *A61B 17/00*  (2006.01)
  *A61B 90/00*  (2016.01)

(52) U.S. Cl.
  CPC .............. *A61N 7/02* (2013.01); *A61B 8/485* (2013.01); *A61B 8/5223* (2013.01); *A61B 8/54* (2013.01); *A61B 8/587* (2013.01); *A61B 2017/00084* (2013.01); *A61B 2090/378* (2016.02)

(58) Field of Classification Search
  USPC ................................................. 600/437–439
  See application file for complete search history.

(56) References Cited

U.S. PATENT DOCUMENTS

| | | | |
|---|---|---|---|
| 2002/0010399 A1* | 1/2002 | Konofagou et al. | 600/449 |
| 2007/0049824 A1* | 3/2007 | Konofagou et al. | 600/437 |
| 2007/0106157 A1* | 5/2007 | Kaczkowski et al. | 600/438 |
| 2008/0081993 A1* | 4/2008 | Waki | A61B 5/02007 600/438 |
| 2009/0105588 A1* | 4/2009 | Emelianov et al. | 600/438 |

OTHER PUBLICATIONS

Liu et al. ("Instantaneous Frequency-based Ultrasonic Temperature Estimation During Focused Ultrasound Thermal Therapy", Ultrasound in Med. & Biol., vol. 35, No. 10, pp. 1647-1661, Oct. 2009).*
Moreno et al. ("Noninvasive temperature estimation in tissue via ultrasound echo-shifts. Part II. In vitro study", J. Acoust. Soc. Am., Oct. 1996).*
Pernot et al. ("Temperature Estimation Using Ultrasonic Spatial Compound Imaging", IEEE, vol. 51, No. 5, May 2004).*
Lin, Ming-Shi et al., Integration of Ultrasonic Temperature Estimation/Elastography in the Monitoring of High-Intensity Focused Ultrasound Therapy, 2009 International Symposium on Biomedical Engineering, Taipei, Taiwan, Dec. 10-11, 2009.

* cited by examiner

*Primary Examiner* — Amanda Lauritzen Moher
*Assistant Examiner* — Shahdeep Mohammed
(74) *Attorney, Agent, or Firm* — Bacon & Thomas, PLLC

(57) ABSTRACT

The invention disclosed a high-intensity focused ultrasound thermal ablation apparatus having integrated temperature estimation and elastography for thermal lesion determination and the method thereof, using the different power to burn by the same focused ultrasound transducer, and then using the apparatus to measure the temperature and elasticity estimating by the relevant analysis method.

8 Claims, 7 Drawing Sheets

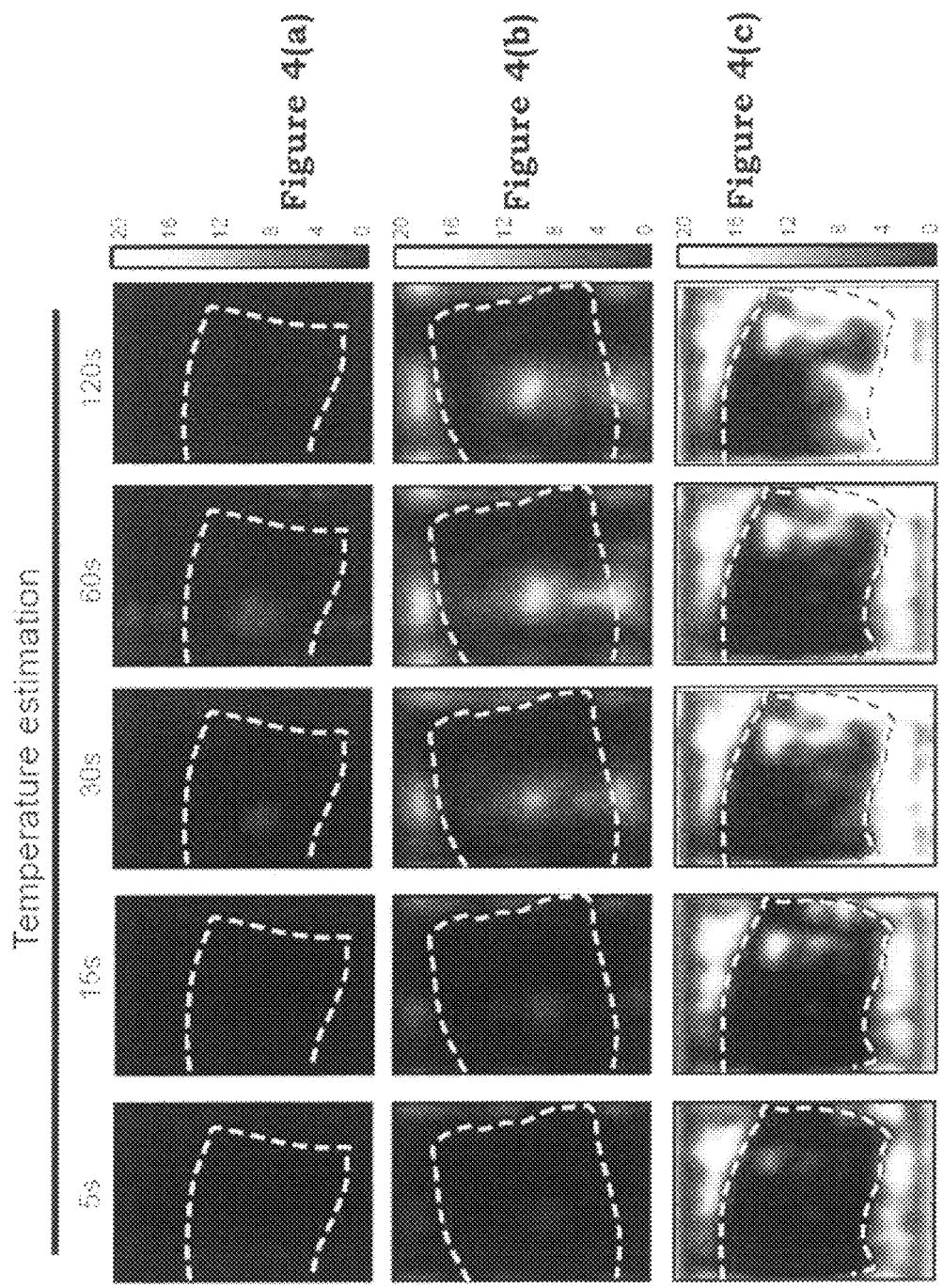

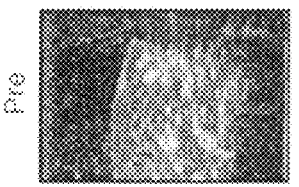
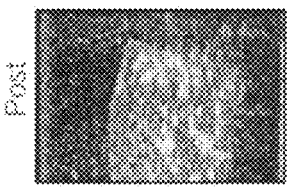
Figure 5(a)
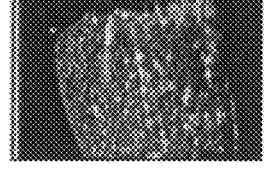
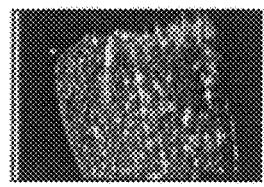
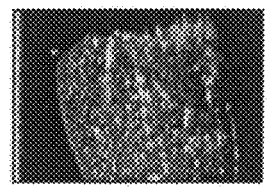
Figure 5(b)
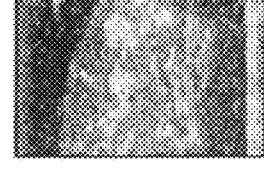
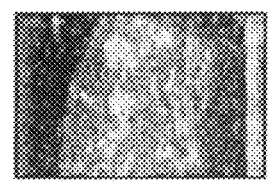
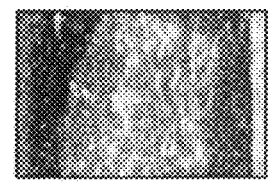
Figure 5(c)

HIGH-INTENSITY FOCUSED ULTRASOUND THERMAL ABLATION APPARATUS HAVING INTEGRATED TEMPERATURE ESTIMATION AND ELASTOGRAPHY FOR THERMAL LESION DETERMINATION AND THE METHOD THEREOF

BACKGROUND OF THE INVENTION

1. Field of the Invention

The invention is related to an ultrasound system having the real-time monitored apparatus and the method thereof, particularly to a high-intensity focused ultrasound thermal ablation apparatus having integrated temperature estimation and elastography for thermal lesion determination and the method thereof.

2. Description of the Prior Art

In recent years, the noninvasive method has been paid more attention in the clinical medical therapy. The ultrasound thermal therapy is gradually matured. The ultrasound has very good penetrating property in human tissue, which is able to transport the energy to deep tissue, thus it can be widely applied in the noninvasive method, such as the tissue lesion to repress the cancer cells, and the suppression of tumor cells etc. The high-intensity focused ultrasound therapy (HIFU) is a kind of ultrasound thermal therapy technique, basically using the high-intensity focused thermal ultrasound to concentrate the energy of the ultrasound. After the energy of ultrasound is focused, the temperature of tissue at the focus region is suddenly raised to above 70° C. The protein of the cell will be denatured at this temperature, thus the tumor can be burnt. Then, the ill tissue will be killed in order to achieve the goal of killing cancer cells.

In the ultrasound thermal therapy process, in order to control the heating degree to avoid injuring the normal tissue around the cell and effectively understand the dimension and the relevant position of thermal lesion after heating, assess the temperature change at large area and lesion range after heating, a monitoring system becomes very important. If the "thermal therapy" is carried out under a situation without any monitoring system, the clinical physician will be unable to judge the heating position and temperature change inside the tissue accurately. It will also be unable to identify the thermal lesion of tissue after heating. Thus the danger degree of the therapeutical process will be increased, and the application of thermal therapy will be limited clinically.

In the monitoring system of ultrasound thermal therapy technique at present, there both are the "ultrasound temperature imaging technique" and the "elastography technique".

Wherein, the "ultrasound temperature imaging technique" uses the ultrasound image in the approximate linear range as the shift quantity to estimate the temperature change. However, if the temperature difference is too high and the object is deformed, it will be unable to estimate the position of thermal lesion correctly. When the thermal expansion is occurred in the tissue, and when the relationship between sound speed and temperature is nonlinear, it will also be unable to estimate temperature change accurately. The echo time displacement tracking way can be used to obtain the dynamic and real-time temperature change in the high-intensity focused ultrasound therapy. However, the limiting condition is that the temperature cannot exceed the linear region of sound speed and temperature (below 50° C.). When the temperature exceeds the critical region, the accuracy of temperature estimate will be lost, due to the change of physical properties, such as permanent tissue destruction, thermal sound lens effect etc.

The "elastography technique" uses the compression or vibration of tissue to estimate the elastic property inside the tissue, but higher noise may be produced around the tissue. Due to the "elastography technique" has high sensitivity for the elastic change of tissue, thus the technique is very suitable to label the real necrotic tissue region after burning. However, limited to poorer anti-noise ability of "elastography technique", the elastic change of necrotic tissue only being contrasted under the necrotic tissue condition has been confirmed. The position and dimension of thermal lesion can only be estimated when the hardness difference is more significant. Unlike the ultrasound temperature imaging technique, it does not have the continuous monitoring ability in the whole therapy process.

Therefore, in order to raise the efficiency of temperature measurement and elastic measurement, it is necessary to develop innovative ultrasound technique, in order to reduce the research and development time and relevant manufacturing cost.

SUMMARY OF THE INVENTION

The purpose of the invention is disclosed to a high-intensity focused ultrasound thermal ablation apparatus having integrated temperature estimation and elastography for thermal lesion determination and the method thereof, in order to improve the imaging and measurement performance.

The invention uses the ultrasound echo signal temperature estimating system, and uses the sound speed change of ultrasound caused by the temperature as the relevant analysis method and instantaneous frequency measurement technique.

The invention collects the elastography technique by using the compression method to form the phase shift displacement of the ultrasound in the different tissue, and analyze the tissue change at before-and-after burnt by the relevant analysis method.

The invention uses the integrated ultrasound temperature image to assess the correct position of initial temperature rise in the tissue. When the temperature exceeds the estimating range (beyond the approximating linear region), the thermal lesion range of burnt tissue can be detected by the elastic image, due to denature and strain change of tissue after heating.

The invention can apply the result of temperature and elasticity estimating to the clinical image ultrasound. Upon carrying out the thermal operation, not only the cross-sectional image of tissue can be obtained, but also the functions of position detection, temperature monitor and elasticity estimating can be got through mathematical calculation, and the integrated ultrasound temperature and elasticity estimating of ultrasound meter can be increased greatly.

On one hand, the invention can understand the heating position and initial temperature rise during the heating process. On the other hand, the thermal lesion can be estimated after heating. After two techniques are integrated, the accuracy for the dimension of thermal lesion can be improved.

This technique uses the same technological core of mathematical calculation to carry out ultrasound temperature estimating and ultrasound elasticity estimating, and integrate the result of temperature and elasticity estimating, in order to increase the estimating accuracy of lesion area.

Therefore, the advantage and spirit of the invention can be understood further by the following detail description of invention and attached Figures.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 4(a), FIG. 4(b), and FIG. 4(c) show the three temperature curves.

FIG. 5(a), FIG. 5(b), and FIG. 5(c) show the B-mode temperature and elasticity maps pre- and post-heating.

DESCRIPTION OF THE PREFERRED EMBODIMENT

The invention is disclosed to a high-intensity focused ultrasound thermal ablation apparatus having integrated temperature estimation and elastography for thermal lesion determination and the method thereof, in order to improve the imaging and measurement performance.

Figure 1:
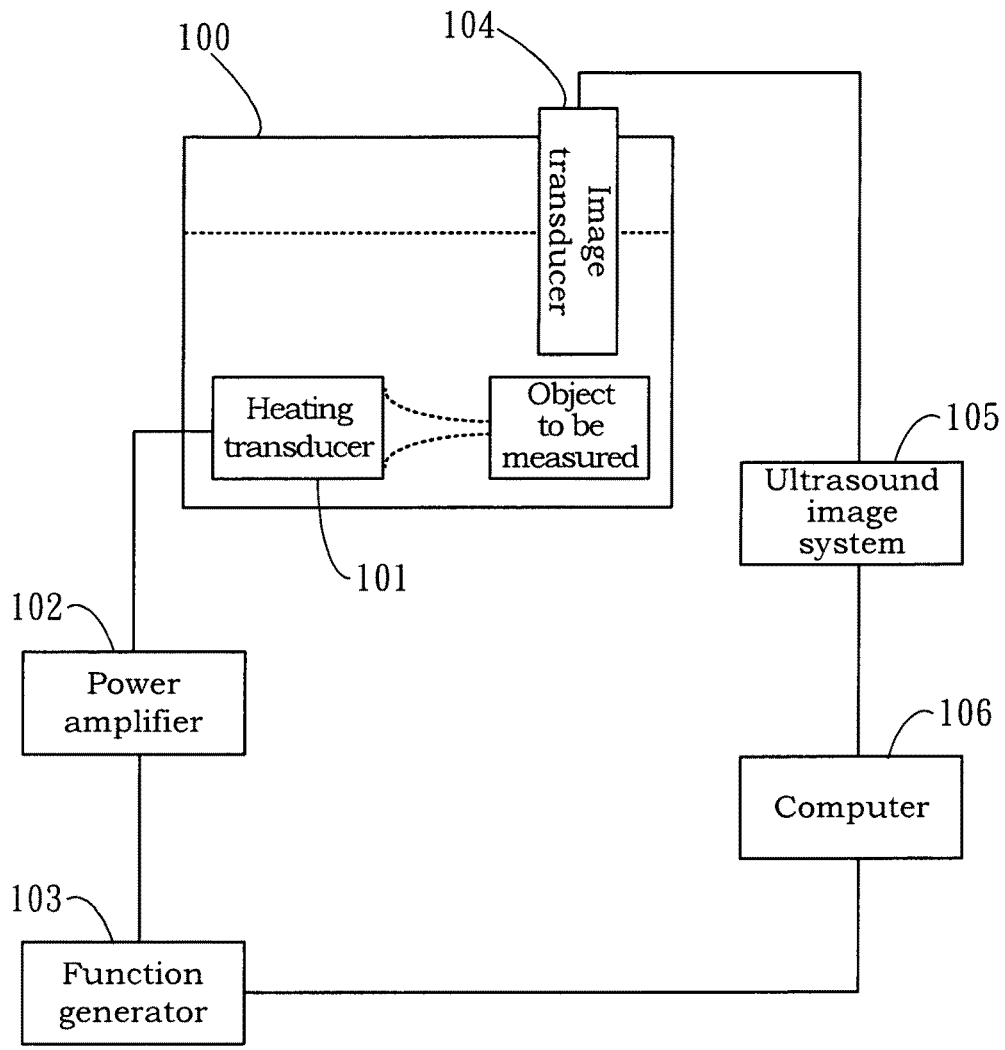
FIG. 1 is a graph illustrating a high-intensity focused ultrasound thermal apparatus with integrated ultrasound temperature-change and elasticity-change of the invention.

The high-intensity focused ultrasound thermal ablation apparatus having integrated temperature estimation and elastography for thermal lesion determination of the invention is shown in FIG. 1 is divided into the heating system and the measurement system. Another, the measurement system comprises the temperature image acquisition and the elasticity image acquisition.

The a high-intensity focused ultrasound thermal ablation apparatus having integrated temperature estimation and elastography for thermal lesion determination of the invention is shown in FIG. 1. It comprises water tank 100, high intensity focused ultrasound (HIFU) transducer 101 (frequency=2 MHz, diameter=35 mm, curvature radius=55 mm; Sonic Concepts Inc., Bothell, Wash., USA), power amplifier 102 (150A100B, Amplifier Research, Souderton, Pa., USA), signal generator 103 (33220A, Agilent, Palo Alto, Calif., USA), ultrasound imaging probe 104, which is a linear array with operating frequency 5 MHz; BW 100%, frame rate 33 Hz, 128 A-lines of RF data output, sampling rate 4 points/wavelength and FOV 38 mm (width) 50 mm (depth); diagnostic ultrasound imaging system 105 (Model T-3000; Terason Inc., Northborough, Mass., USA), which is employed to collect RF data for offline analysis; and computer 106.

The high intensity focused ultrasound transducer 101 connects to the power amplifier and the signal generator 103 to form the heating system. The ultrasound imaging probe 104 connects to the diagnostic ultrasound imaging system 105 and the computer 106 to form the measurement system. The measurement system and the heating system are connected each other. The above-mentioned high intensity focused ultrasound transducer 101 and the ultrasound imaging probe 104 both are put in the water tank 100 for use.

In addition, a power monitor (4421, BIRD Inc., Solon, Ohio, USA) is used (not shown) as well. These above-mentioned modules produced electrical power in the range 5 W to 25 W. The electrical-to-acoustic efficiency of the high intensity focused ultrasound (HIFU) transducer 101 is estimated to be 70% using a force-balance meter (Model UPM-DT-1, Ohmic Instruments, Easton, Md., USA). The ultrasound imaging probe 104 as FIG. 1 is mounted on a positioning table (allowing translation along the axis of the imaging probe, minimum resolution=30 μm) and then attached to the top surface of the phantom. This arrangement provides precise manual control over the compression displacement.

Before any further processing of the acquired A-lines, a simple linear interpolation (this choice of algorithms reflects a compromise between computation time and the required resolution for temperature estimation) is applied to increase the sampling rate by a factor of 10. Since the ultrasonic imagers do not support real-time data acquisition, people only collected the RF data. All thermal images are reconstructed offline from the various datasets.

The degassed water should be put into the water tank 100 of the invention to avoid the empty hole effect and influence the result, and the water temperature should be controlled at about 30° C. The invention accumulates the string wave energy to the focus place, in order to achieve the heating effect.

The invention uses the general purpose interface bus (GPIB) transmit device to connect the high intensity focused ultrasound transducer 101 (the central frequency of transducer is 2 MHz, and the focus depth of transducer is 5 nm), the power amplifier 102, the function generator 103, the computer 106, the diagnostic ultrasound imaging system 105 and the ultrasound imaging probe 104. The "Matlab computer program" software installed in the computer 106 is used to control the signal generator 103 to generate the signal. The signal passes through the power amplifier 102 to activate the high intensity focused ultrasound transducer 101. Thus the output power of ultrasound can be adjusted. High temperature is generated at the focus of high intensity focused ultrasound transducer 101 to heat the "object to be measured" in the water tank 100.

The "ultrasound image system" of the invention has a linear imaging probe 104 with 128 elements. The ultrasound imaging probe 104 combines with the diagnostic ultrasound imaging system 105 to measure the "cross-sectional image" and "echo signal" of heating position (object to be measured) accurately upon ultrasound thermal therapy. The ultrasound image of cross-sectional plane and the signal of image are obtained separately. Analyze the phase shift displacement caused by the corresponding "A-line" signal of image under each temperature time. The estimating of two-dimensional temperature image can be obtained. Then it can carry out the vertical compression of signal, wherein the minimum compression scale will be 0.01 mm. Thus it can control the compression displacement to carry out the elasticity measurement.

When the high intensity focused ultrasound transducer 101 (abbreviated as heating transducer) is used to carry out partial heating, the ultrasound signal of the high intensity focused ultrasound transducer 101 will interfere with the radio frequency signal produced by the above-mentioned "ultrasound image system" at the same time. In order to avoid the interference of data access upon heating, it is necessary to use the intermittent heating to activate the high intensity focused ultrasound transducer 101 and the ultrasound imaging probe 104, so that the object can be heated and the ultrasound echo datum of each temperature can be obtained at the same time.

The operation method of the invention is shown in FIG. 1. First, use the computer 106 to control the signal generator 103 to produce the cluster wave. The energy of cluster wave is amplified by the power amplifier 102, which is transported to the high intensity focused ultrasound transducer 101 to focus on heating the "object to be heated". After the heating, compress the ultrasound imaging probe 104 (about 5 seconds, the temperature of water tank 100 is fixed at 30° C.) to obtain the image signal. It is transported to the computer 106 for image processing through the diagnostic ultrasound imaging system 105.

Figure 2:
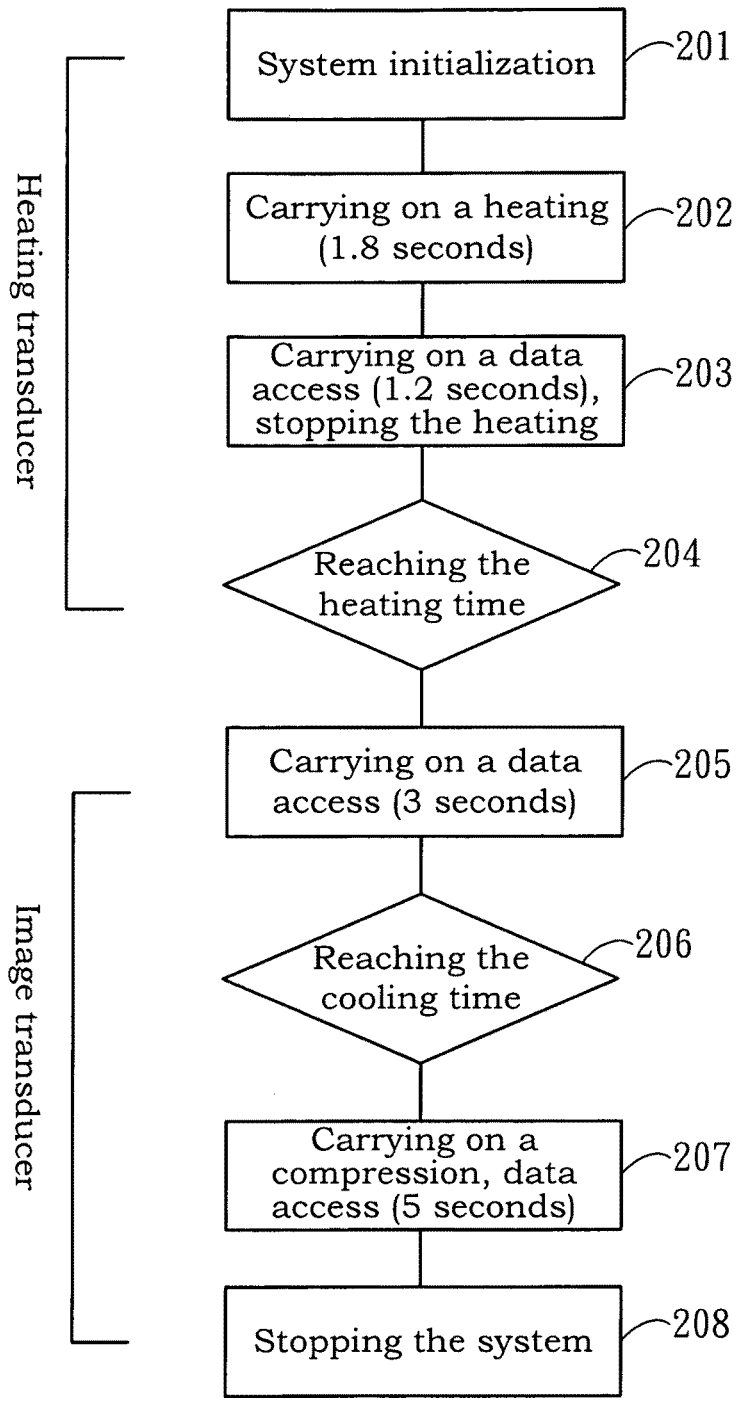
FIG. 2 is a graph illustrating the method for data access by the intermittent heating.

The method for data access by the intermittent heating is shown in FIG. 2. Firstly, the system is initialized 201. Then it is heated 202 for about 1.8 seconds. The data access is continued 203 for about 1.2 seconds, and the heating will be stopped now. Then the heating time is up 204. The above-mentioned steps are the operation steps for heating the transducer.

Still as shown in FIG. 2, the data access is continued 205 for about 3 seconds. Then the cooling time is arrived 206. Compress it to access data 207 for about 5 seconds. The above-mentioned steps are the operation steps of image transducer.

Figure 3:
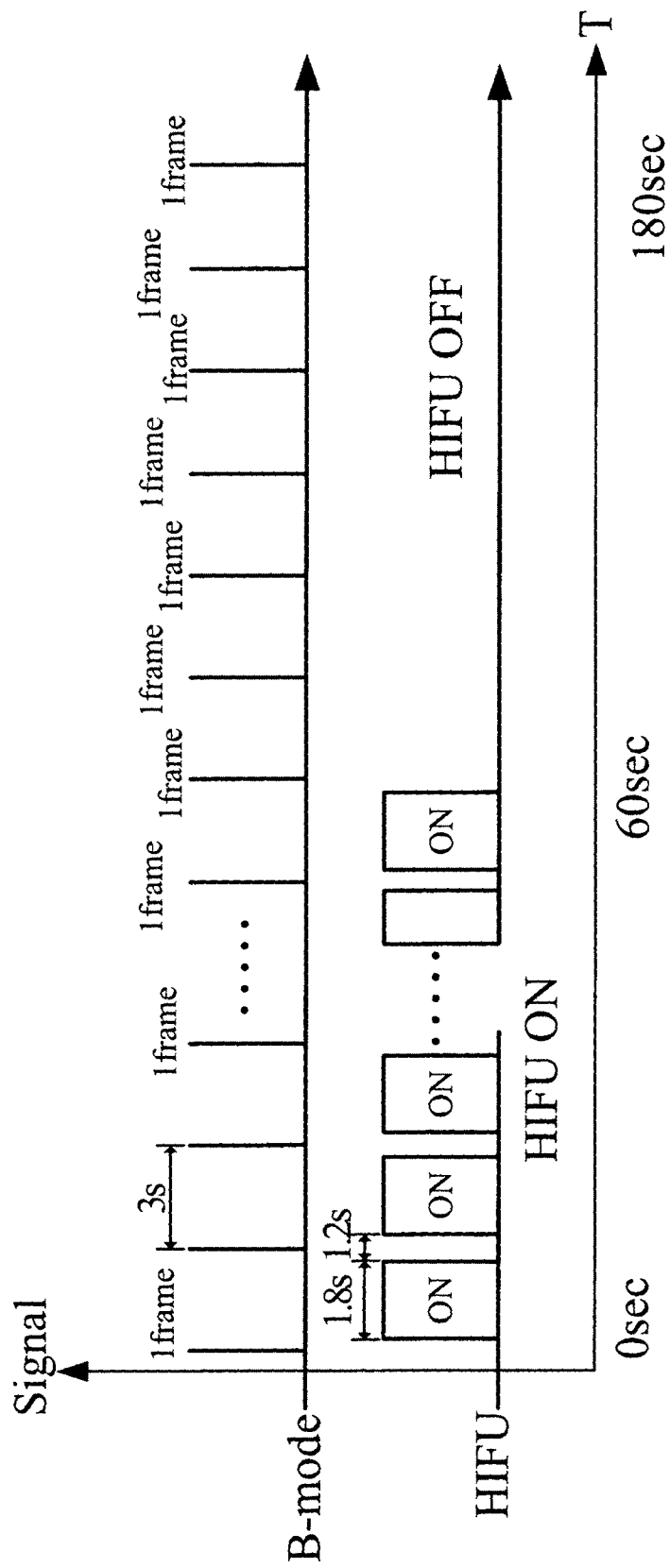
FIG. 3 is a graph illustrating a detailed embodiment for the method for data access by the intermittent heating of the invention.

FIG. 3 is a graph illustrating a detailed embodiment for the method for data access by the intermittent heating of the invention.

After it is heated for 1.8 seconds, then it is stopped for 1.2 seconds, which become a cycle. The image is acquired upon the heating is stopped, 20 cycles are carried on, thus the total time is 60 seconds. During the cooling time, a datum is acquired per 3 seconds. There are 60 cycles for total procedure including the heating and cooling.

The mathematical calculation principle of the invention is described in detail as follows:

Theoretical Basis of the Heat- and Compression-Induced Strain Changes:

The method of estimating temperatures from echo time shifts has been detailed previously. Assuming the temperature change $\Delta T(z)$ in tissue at any RF signal location $z=z_n$ is linearly proportional to the displacement between two corresponding points of the RF signal and echo time series:

$$\Delta t(z) = t(z)|_{z=z_n}^1 - t(z)|_{z=z_n}^2.$$

This assumption is valid provided that we only consider temperature-induced changes to the sound speed and thermal expansion of the tissue; any nonlinear tissue changes are neglected. The relationship between temperature and time displacement is then given by $$\Delta T(z) \propto \left( \frac{1}{\alpha(z) - \beta(z)} \right) \cdot \frac{\partial}{\partial z} \Delta t(z), \quad \text{equation (1)}$$

where $\alpha(z)$ is the linear coefficient of thermal expansion of the medium at axial depth z, $$\beta(z) = \frac{1}{c_0(z)} \cdot \frac{\partial c(z, T)}{\partial T} \bigg|_{T=T_0}$$

is defined as the coefficient of thermally induced sound speed, and T is the temperature.

For small temperature changes (between 30 and 50° C.), $\beta(z)$ is fixed for a specific tissue type and no significant thermal expansion occurs. Equation (1) can then be simplified as follows:

$$\Delta T(z) \approx k_t \cdot \frac{\partial}{\partial z} \Delta t(z). \quad \text{equation (2)}$$

When tissue undergoes external compression, the longitudinal strain change can be estimated by:

(1) acquiring RF echo signals from the region targeted for FUS ablation, thereby obtaining a pair of arrival times denoted $t(z)|_{z=z_1}^1$ and $t(z)|_{z=z_1}^1$ for each point z;

(2) compressing the tissue by a small amount using a transducer (or a transducer/compressor module); and (3) acquiring another set of RF echoes in order to have a second pair of arrival times for each point, denoted $t(z)|_{z=z_1}^2$ and $t(z)|_{z=z_1}^2$. The axial strain change $\Delta E(z)$ can then be estimated as $$\Delta E(z) \propto \frac{\left(t(z)|_{z=z_1}^1 - t(z)|_{z=z_2}^1\right) - \left(t(z)|_{z=z_1}^2 - t(z)|_{z=z_1}^2\right)}{\left(t(z)|_{z=z_1}^1 - t(z)|_{z=z_2}^1\right)} \quad \text{equation (3)}$$

which can be rearranged as follows:

$$\Delta E(z) \approx k_e \cdot \frac{\left(t(z)|_{z=z_1}^1 - t(z)|_{z=z_1}^2\right) - \left(t(z)|_{z=z_2}^1 - t(z)|_{z=z_2}^2\right)}{\left(d_{z=z_1} - d_{z=z_2}\right)}. \quad \text{equation (4)}$$

Here $(d_{z=z_1} - d_{z=z_2})$ represents a small distance between $z_1$ and $z_2$ in the estimation region. Since $(t(z)|_{z=z_1}^1 - t(z)|_{z=z_1}^2)$ and $(t(z)|_{z=z_2}^1 - t(z)|_{z=z_2}^2)$ are the echo time shifts, the above equation can be simplified to a statement that the derivative of the time shift is proportional to the external compression:

$$\Delta E(z) \approx k_e \cdot \frac{\partial}{\partial z} (\Delta t(z)) \quad \text{equation (5)}$$

It should be noted that although the echo time shift and its derivative in equation (3) and equation (5) represent different physical effects (the former relates to the strain induced by the temperature change, and the latter relates to the elasticity change induced by the compression force), the numerical calculations of these two processes are identical.

Numerical Estimation of the Heat- and Compression-Induced Strain Changes:

The strain changes presented in equation (2) and equation (5) are based on echo time shifts, which can be estimated by computing a 1-D cross-correlation on paired RF A-lines. The strains can then be calculated using the numerical derivative of the time shift:

$$\frac{\partial}{\partial z} (\Delta t(z)) \bigg|_{z=z_n} \approx \frac{\Delta t(z_{n+1}) - \Delta t(z_{n-1})}{z_{n+1} - z_{n-1}} \quad \text{equation (6)}$$

For both methods, the cross-correlation processing windows are 6λ (λ=wavelength) and adjacent windows have an overlap of 75%. These settings are based on our previously reported optimal values. To further smooth the differentiated data (after applying equation (6)) and reduce Gaussian noise in the image, applied to a 2D median filter (3×3 data points). All the calculations were implemented in Matlab (Mathworks Inc., Natick, Mass., USA) and executed on a personal computer (Intel Core-2-Duo CPU, T5800, at 2 GHz). The cross-correlation algorithm is used and provided by Matlab.

The above-mentioned algorithm technique is a method for the high-intensity focused ultrasound thermal ablation apparatus having integrated temperature estimation and elastography for thermal lesion determination. The steps are described in detail as follows:
1. Reconstruct the obtained ultrasound data into the raw data. The ultrasound data include a stress source caused by the temperature and a stress source caused by the pressure.
2. There are 128 signals in the reconstructed raw data. These 128 signals are diced into a plurality of fragments. An echo time shift is used to calculate the shift of every fragment to obtain the stress source.
3. Use the relevant analysis method to compare the shift of every fragment before and after the application of stress, in order to obtain the echo time shift. In the temperature image aspect, the echo time shift represents the time shift caused by the heating in a region. In the elasticity image aspect, the echo time shift represents the displacement caused by the compression in a region.
4. A shield of the temperature image is used to isolate a noise in the elasticity image. When the echo time shifts of front fragment and rear fragment are subtracted, the slope (the result of first differentiation) will be obtained. It represents the change amount of adjacent fragments. When the correction coefficient is introduced, the strain image can be obtained, including the ultrasound temperature-change image and the ultrasound elasticity-change image. The temperature-change image represents the temperature rising effect of adjacent fragments. The elasticity-change image represents the displacement caused by the stress.

In the invention, the phantom that is made of ex vivo swine liver tissue embedded inside polyacrylamide gel. The advantage of polyacrylamide is that it solidifies at room temperature. The liver tissue sample is vacuumed, diced to a suitable size, placed in a container with the following dimensions=60×60×100 mm. Finally, the container is filled with polyacrylamide to pave the tissue sample. After solidification, the ex vivo tissue phantoms provide an ideal surface for compression or focused ultrasound sonication. The ex vivo tissue phantom are conducted to evaluate the performance of the unified computational kernel on the basis of contrast analysis and the prediction of thermal lesion size. Before sonication, it acquired an initial set of RF data with compression. During focused ultrasound heating, the RF-signal acquisition process was identical to that used in the type I experiments. It conducted experiments at focused ultrasound powers of 5 W, 15 W, and 25 W, each time with a heating duration of 60 s. After 10 minutes of focused ultrasound sonication, it acquired another set of RF data with compression to provide a second elasticity map. The process of RF data acquisition in this stage is identical to the first compression. Finally, the ex vivo tissue phantoms are diced for photography to compare the images to the real necrotic tissue regions.

FIG. 4(a), FIG. 4(b), and FIG. 4(c) demonstrate three typical heating cases at focused ultrasound powers of 5 W, 15 W, and 25 W. At the 5-W level, temperature elevation becomes apparent after 30 s of heating and the temperature buildup is greater than 5° C. However, neither the echogenic B-mode image nor the elastography exhibits much change in contrast, indicating that no necrosis occurred (this is confirmed after the experiments by examining the dissected tissues). At the 15-W setting, the temperature build-up is more rapid and more apparent (>10° C. within 20 s). Thermal lensing artifacts are visible and become most apparent starting from 30 s. No change is found in the B-mode image, however, so little strain change is produced (less than 0.5% of strain difference, and the lesion is confirmed by tissue dissection). It also noted compression-induced strain artifacts neighboring the target position, which made determination of the true necrotic region challenging. The 25-W setting created a more extreme temperature change (>20° C. within 15 s) and strain change (up to 1%), and generated the largest necrosed lesion (confirmed in tissue dissection). However, the thermal lensing and compression-induced strain artifacts were also the most extreme among the cases.

The first two columns in FIG. 5 (including FIG. 5(a), FIG. 5(b), and FIG. 5(c)) show the B-mode diagram before and after heating to compare with the temperature imaging shown in FIG. 4 (including FIG. 4(a), FIG. 4(b), and FIG. 4(c)), and the elastography diagram before and after heating cases was shown in the third and the fourth column in FIG. 5 (including FIG. 5(a), FIG. 5(b), and FIG. 5(c)) on the display of computer 106 for the operation of the high-intensity focused ultrasound thermal ablation apparatus having integrated temperature estimation and elastography for thermal lesion determination of the invention. The area of real necrotic tissue region is then estimated and shown in the last fifth column in FIG. 5 (including FIG. 5(a), FIG. 5(b), and FIG. 5(c)), and compared to the temperature image, the elasticity image, and the integrated image.

Figures 6A, 6B, 6C:
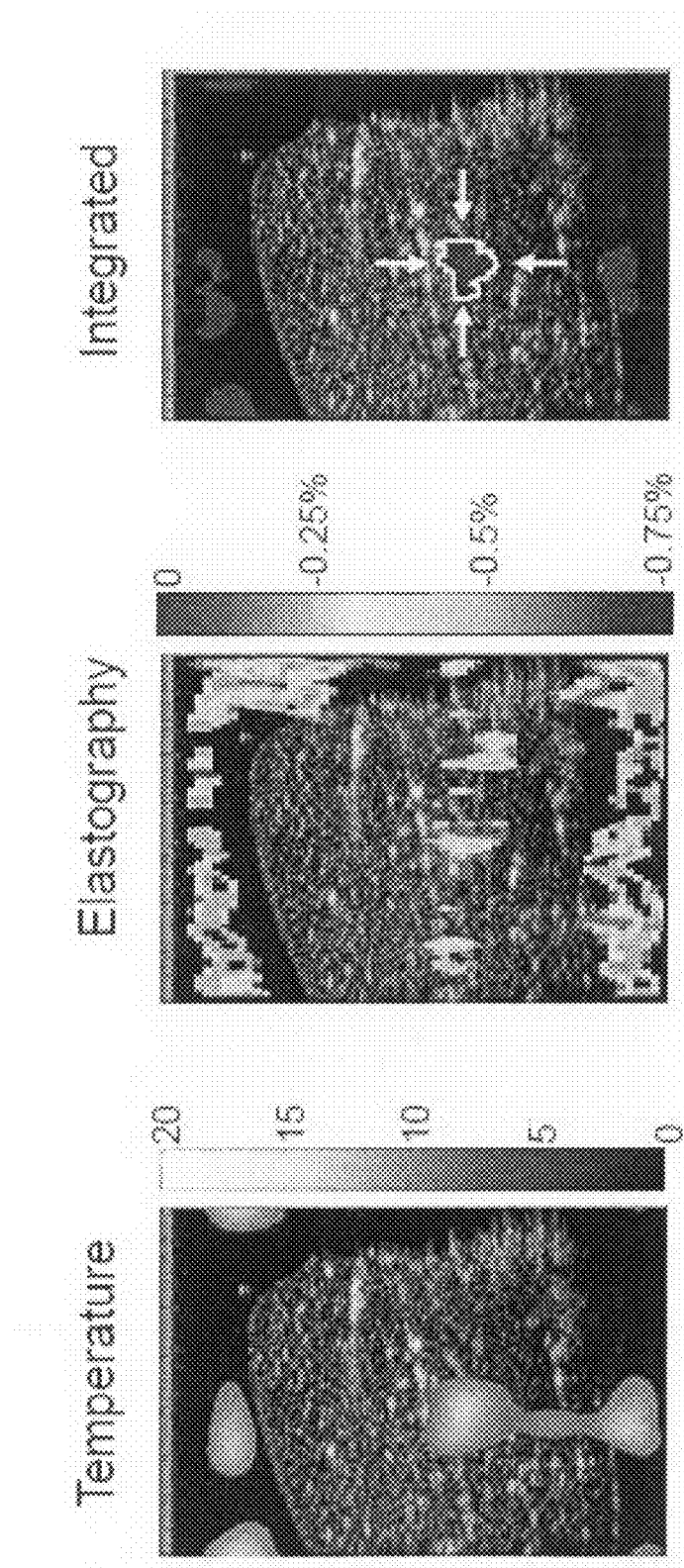
FIG. 6(a) and FIG. 6(b) show the fused temperature imaging and elastography images on B-mode sonography.
FIG. 6(c) shows that the regions selected after taking into account both constraints.

Furthermore, the ex-vivo tissue phantom experiments evaluate the performance of the invention in monitoring temperature and predicting the volume of necrosed tissue. FIG. 6(a) and FIG. 6(b) show the fused temperature imaging (>10° C.) and elastography (>0.5% strain change) images on B-mode sonography. These figures show that the artifacts in the temperature and elasticity maps appear in different locations. The regions selected after taking into account both constraints (regions >10° C. and strain changes >0.5%) are shown in FIG. 6(c).

Figure 6F:
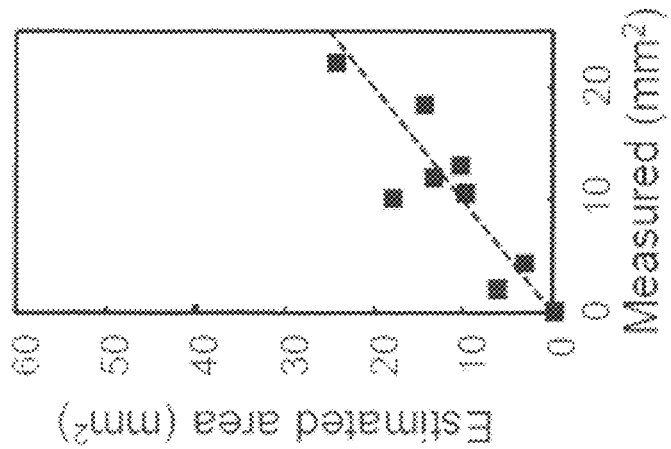
FIG. 6(d), FIG. 6(e) and FIG. 6(f) show the necrotic tissue dimensions estimated from temperature mapping only, post-heating elastography only, and their intersection respectively.
Figure 6E:
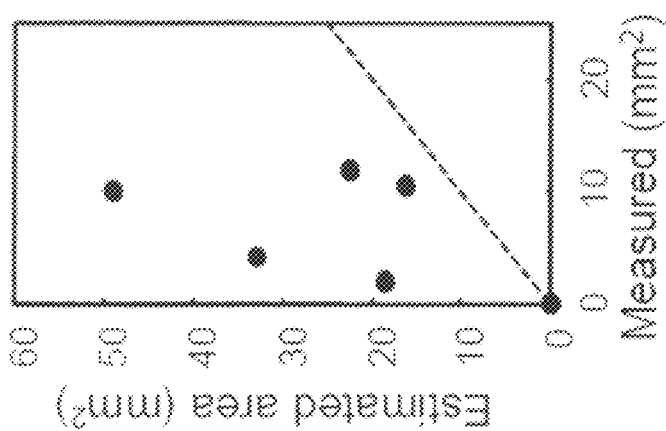
Figure 6D:
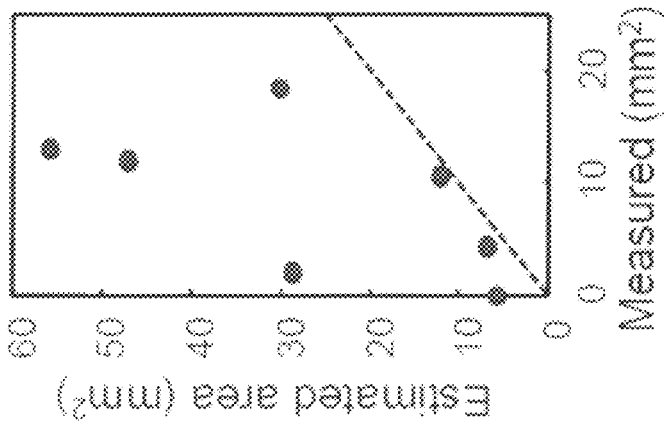

FIG. 6(d), FIG. 6(e) and FIG. 6(f) show the necrotic tissue dimensions estimated from temperature mapping only (the regions with temperature elevation change >10° C.), post-heating elastography only (strain change >0.5%), and their intersection (both >10° C. temperature elevation and >0.5% strain change) respectively. FIGS. 6(d) and 6(e) show that both individual approaches over-estimate the lesion dimensions. However, when the two criteria are combined, the estimated necrotic dimension is profoundly improved (FIG. 6(f). The dimensions estimated by the invention are all very close to those measured after dissecting the phantoms (r2=0.90).

From the examples being demonstrated above, the procedure can be concluded as follows. After the "high-intensity focused ultrasound therapy" is activated, if the ultrasound temperature estimating is used as the monitoring way, the real-time temperature image during heating process can be obtained. When the temperature exceeds the linear estimating range and after the operation is finished, the ultrasound elasticity image can be used to confirm the real necrotic tissue region and calculate the volume of the real necrotic tissue region.

As for the analysis aspect of the elasticity image, because the hardness of tissue before and after the compression is different, it will cause the difference of tissue denature displacement, which also represents the time difference of echo signal in the physical meaning. As for the calculation way of echo time shift, the ultrasound A-line before and after time shift is analyzed relevantly. The relevant analysis uses the Fourier theory of to estimate the time shift mainly. First, acquire the corresponding linear fragments, and use the convolution to carry out the relevant analysis, the shift of maximum peak value can be used to estimate the time shift of two functions.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A method for operating a high-intensity focused ultrasound (HIFU) thermal ablation apparatus having functions of integrated temperature estimation and elastography for thermal lesion determination comprising:
   reconstructing an ultrasound data into raw data using the high-intensity focused ultrasound (HIFU) thermal ablation apparatus;
   dicing the raw data into a plurality of fragments and using an echo time shift to calculate a shift of every fragment using the high-intensity focused ultrasound (HIFU) thermal ablation apparatus, wherein the raw data comprise 128 signals;
   using the high-intensity focused ultrasound (HIFU) thermal ablation apparatus to compare the shift of every fragment before and after an application of stress in order to obtain and acquire a temperature image and an elasticity image; and
   obtaining a strain image including an ultrasound temperature-change image and an ultrasound elasticity-change image by integrating the temperature image and the elasticity image,
   wherein the ultrasound temperature-change image being defined as a temperature rising effect, the ultrasound elasticity-change image being defined as a displacement caused by the stress,
   wherein a relationship between a temperature and a time displacement is given by $$\Delta T(z) \propto \left(\frac{1}{\alpha(z) - \beta(z)}\right) \cdot \frac{\partial}{\partial z} \Delta t(z), \quad \text{equation (1)}$$

wherein $\alpha(z)$ is a linear coefficient of a thermal expansion of a medium at an axial depth z, $$\beta(z) = \frac{1}{c_0(z)} \cdot \left.\frac{\partial c(z,T)}{\partial T}\right|_{T=T_0}$$

being defined as a coefficient of thermally induced sound speed, and T is a temperature,
   wherein equation (1) is simplified for small temperature changes as $$\Delta T(z) \approx k_t \cdot \frac{\partial}{\partial z} \Delta t(z), \quad \text{equation (2)}$$

wherein $k_t$ is a first constant,
   wherein when a tissue undergoing external compression, a longitudinal strain change is estimated comprising the steps:
     acquiring radio frequency ("RF") echo signals from a region targeted for focused ultrasound ("FUS") ablation, obtaining a pair of arrival times denoted $t(z)|_{z=z_1}^1$ and $t(z)|_{z=z_1}^1$ for each point z;
     compressing the tissue by a small amount using a transducer; and
     acquiring a set of RF echoes in order to have a second pair of arrival times for each point, denoted $t(z)|_{z=z_1}^2$ and $t(z)|_{z=z_1}^2$, and estimating an axial strain change $\Delta E(z)$ as $$\Delta E(z) \propto \frac{\left(t(z)|_{z=z_1}^1 - t(z)|_{z=z_2}^1\right) - \left(t(z)|_{z=z_1}^2 - t(z)|_{z=z_2}^2\right)}{\left(t(z)|_{z=z_1}^1 - t(z)|_{z=z_2}^1\right)}, \quad \text{equation (3)}$$

wherein said equation (3) is rearranged as $$\Delta E(z) \approx k_e \cdot \frac{\left(t(z)|_{z=z_1}^1 - t(z)|_{z=z_1}^2\right) - \left(t(z)|_{z=z_2}^1 - t(z)|_{z=z_2}^2\right)}{(d_{z=z_1} - d_{z=z_2})}, \quad \text{equation (4)}$$

wherein $(d_{z=z_1} - d_{z=z_2})$ represents a small distance between $z_1$ and $z_2$ in an estimation region, $(t(z)|_{z=z_1}^1 - t(z)|_{z=z_1}^2)$ and $(t(z)|_{z=z_2}^1 - t(z)|_{z=z_2}^2)$ being the echo time shifts, and $k_e$ is a second constant,
   simplifying said equation (1), said equation (2), said equation (3), and said equation (4), to a statement that a derivative of the time shift being proportional to an external compression as $$\Delta E(z) \approx k_e \cdot \frac{\partial}{\partial z}(\Delta t(z)), \quad \text{equation (5)}$$

wherein strain changes presented in said equation (2) and said equation (5) being based on the echo time shifts, which is estimated by computing a 1-D cross-correlation on paired RF A-lines, wherein said strain changes are calculated using a numerical derivative of said time shifts as $$\left.\frac{\partial}{\partial z}(\Delta t(z))\right|_{z=z_n} \approx \frac{\Delta t(z_{n+1}) - \Delta t(z_{n-1})}{z_{n+1} - z_{n-1}}. \quad \text{equation (6)}$$

2. The method according to claim 1, further comprising the steps determining a necrotic tissue region and calculating a volume of the necrotic tissue region using the strain image including the ultrasound temperature-change image and the ultrasound elasticity-change image.

3. The method according to claim 1, further comprising the step of heating the tissue using a high intensity focused ultrasound transducer and measuring a cross-sectional image and echo signal of a heating position in the object to be measured using at least said transducer.

4. The method according to claim 3, further comprising the step obtaining an estimate of a two-dimensional temperature image, wherein elasticity measurements are obtained by carrying out a vertical compression of the signal.

5. The method according to claim 3, wherein the external compression of the tissue occurs after a cooling time is reached after the heating the tissue.

6. The method according to claim 3, wherein the heating occurs intermittently.

7. The method according to claim 3, wherein the heating occurs using ultrasound powers of 5 W, 15 W, and 25 W.

8. A method for operating a high-intensity focused ultrasound (HIFU) thermal ablation apparatus having functions of integrated temperature estimation and elastography for thermal lesion determination, wherein, when executed by a processor, comprises the following steps:
  reconstructing an ultrasound data into raw data using the high-intensity focused ultrasound (HIFU) thermal ablation apparatus;
  dicing the raw data into a plurality of fragments and using an echo time shift to calculate a shift of every fragment using the high-intensity focused ultrasound (HIFU) thermal ablation apparatus, wherein the raw data comprise 128 signals;
  using the high-intensity focused ultrasound (HIFU) thermal ablation apparatus to compare the shift of every fragment before and after an application of stress from at least one transducer in order to obtain and acquire a temperature image and an elasticity image; and
  obtaining a strain image including an ultrasound temperature-change image and an ultrasound elasticity-change image by integrating the temperature image and the elasticity image for image processing by a computer of the high-intensity focused ultrasound (HIFU) thermal ablation apparatus,
  wherein the ultrasound temperature-change image is defined as a temperature rising effect and the ultrasound elasticity-change image being defined as a displacement caused by the stress,
  wherein for small temperature changes, the temperature rising effect is defined as $$\Delta T(z) \approx k_t \cdot \frac{\partial}{\partial z} \Delta t(z),$$

wherein $k_t$ is a first constant, and z is an axial depth
  wherein the displacement caused by the stress is defined as an axial strain change $\Delta E(z)$ as $$\Delta E(z) \approx k_e \cdot \frac{\partial}{\partial z} (\Delta t(z)),$$

wherein $k_e$ is a second constant, and
  wherein changes in the strain image are calculated using a numerical derivative of time shifts as $$\left. \frac{\partial}{\partial z}(\Delta t(z)) \right|_{z=z_n} \approx \frac{\Delta t(z_{n+1}) - \Delta t(z_{n-1})}{z_{n+1} - z_{n-1}}.$$

* * * * *